United States Patent [19]
O'Malley et al.

[11] Patent Number: 5,849,477
[45] Date of Patent: Dec. 15, 1998

[54] ASSAYS OF COUP TRANSCRIPTION FACTOR INTERACTIONS IN MAMMALIAN SYSTEMS

[75] Inventors: Bert William O'Malley; Ming-Jer Tsai; Lee-Ho Wang; Sophia Yang Tsai, all of Houston, Tex.

[73] Assignee: Baylor College of Medicine, Houston, Tex.

[21] Appl. No.: 852,731

[22] Filed: Mar. 16, 1992

Related U.S. Application Data

[63] Continuation of Ser. No. 335,405, Apr. 10, 1989, abandoned.
[51] Int. Cl.$^6$ ........................................ C12Q 1/68
[52] U.S. Cl. .............................. 435/6; 435/91.1; 436/811; 530/350; 530/399; 536/23.1; 536/23.5
[58] Field of Search ....................... 435/6, 91.1; 530/350, 530/399; 436/811; 536/23.1, 23.5

[56] References Cited

PUBLICATIONS

Sagami et al: "Identification of two Factors Required for transcription of the Ovalbumin Gene" *Molecular & Cellular Biology* V.6 No. 12 pp. 4259–4267 (Dec. 1986).

Wang et al (I): "Purification and Characterization of Chicken Ovalbumin Upstream Transcription Factor from He La Cells" *Journal of Biological Chemistry* V. 262 No. 33 (Nov. 1987) pp. 16080–16086.

Wang et al (II): "Studies of Coup Transcription Factor From HeLa Cells: Purification and Partial Characterization" *Progress in Clinical Biological Research* V 284 pp. 37–51 (1988).

Dame et al: "Structure of the Gene Encoding the Immuno–dominant Surface Anitgen on the Sporofoite of the Human Malaria Parasite Plasmodium falciparum" *Science* V 225, pp. 593–599 (Aug. 10, 1984).

*Primary Examiner*—Christine M. Nucker
*Assistant Examiner*—Jeffrey Stucker
*Attorney, Agent, or Firm*—Fulbright & Jaworski L.L.P.

[57] ABSTRACT

Multiple methods for measuring the COUP-TF system, including: a method to measure the level of COUP-TF by combining antibodies with biological samples and measuring the resultant antibody/COUP-TF complex; the binding of COUP-TF to promoters by combining biological samples with COUP-TF binding oligonucleotides and measuring the resultant complex or gene synthesis; and a method to measure COUP-TF inducable promoters by combining native COUP-TF with nuclear extracts of biological samples and measuring the resultant complexes. The methods when applied to human biological samples can detect diabetes due to COUP-TF or promoter defects. In addition to the methods for measuring the COUP-TF system and associated diseases, there are also the polyclonal and monoclonal antibodies necessary for the methods. These bind to at least one immunoreactive site on COUP-TF. Furthermore, there is a DNA clone containing the genetic coding regions of the COUP-TF protein.

2 Claims, 3 Drawing Sheets

Figure 1 A&B

ASSAYS OF COUP TRANSCRIPTION FACTOR INTERACTIONS IN MAMMALIAN SYSTEMS This application is a continuation of application Ser. No. 07/335,405, filed Apr. 10, 1989, now abandoned.

FIELD OF THE INVENTION

The present invention relates generally to COUP transcription factor (COUP-TF). More particularly, it relates to a cDNA clone of the gene encoding COUP-TF, antibodies to the COUP-TF, and assays for determining the amount of COUP-TF, its binding ability and its promoter interaction. It also relates to detection of diabetes caused by deficiencies within the COUP-TF system.

BACKGROUND OF THE INVENTION

The chicken ovalbumin upstream promoter transcription factor (COUP-TF) recognizes the sequence GTGTCAAAG-GTCAAA and promotes the transcription of the chicken ovalbumin gene. The COUP sequence has been shown in both in vivo and in vitro studies to be a cis-acting element regulating the expression of the chicken ovalbimin gene. Recognition sequences of the DNA contact sites have been characterized for COUP-TF. COUP-TF is found in a number of different tissues and cell lines including HeLa cells. COUP-TF has been previously purified 200,000 fold from HeLa cells using a combination of conventional and sequence-specific DNA affinity chromatographies. This purified protein is required for accurate initiation of transcription from the ovalbumin gene promoter in a cell free system. Furthermore, S300 II is required for COUP-TF mediated transcription of the ovalbumin gene in vitro. Additionally, it is known that COUP-TF combines specifically to the rat insulin promoter element (RIPE). Interestingly neither the COUP nor RIPE binding sites share sequence similarity.

The procedure of cross-screening cDNA libraries using conserved sequences of receptor genes has generated numerous "receptors" which are members of the steroid receptor superfamily by sequence homology, although their function is not known. COUP-TF has been published as one of these "orphan receptors" cDNA clones and termed ear III. This cDNA clone was obtained from a DNA library by cross-screening with a v-erb A probe.

It is now known that COUP-TF binds to a promoter sequence which is upstream from a variety of genes including the rat insulin gene and the chicken ovalbumin gene. This binding promotes transcription of insulin and ovalbumin proteins. Thus, COUP-TF has a strong regulatory effect in controlling the rate of insulin and ovalbumin synthesis.

Insulin is one of the key peptide hormones in the control or growth and metabolism. A disturbance in insulin biosynthesis or in the response to insulin results in diabetes mellitus. Because of the large number of patients and thus the effects on society, diabetes has been intensely studied. One area that has been actively investigated has been the regulation of translation and the secretion of insulin. This study of gene expression has been facilitated by the availability of techniques to examine the molecule at the DNA level.

The ability to detect defects in insulin regulation systems provides a method for detecting diabetes and for designing and using alternate therapeutic regimens to prevent the onset and to treat diabetes.

The present invention describes new types of assays for measuring insulin promoter and regulating protein defects for diabetes. These new methods of detecting diabetes mellitus provide another tool for examing the fundamental structural defect resulting in the disease and for designing new therapies.

SUMMARY OF THE INVENTION

An object of the present invention is the provision of a method for the detection of insulin promoter defects.

An additional object of the present invention is an assay for the detection of COUP-TF defects.

A further object of the present invention is a method for identifying COUP-TF promoter interaction defects.

An additional object of the present invention is the provision of antibodies for measuring COUP-TF.

A further object of the present invention is the provision of a cDNA clone of the COUP-TF gene.

An additional object of the present invention is the development of the use of the cDNA clone, antibodies, or COUP-TF to detect diabetes mellitus.

Thus, in accomplishing the foregoing objects, there is provided in accordance with one aspect of the present invention a method for measuring COUP-TF level in a biological sample comprising the steps of combining an antibody that binds to at least one antigenic site of COUP-TF with said biological sample; and assaying the biological sample/antibody mixture for antibody binding. One specific embodiment of the method includes measuring an antibody/COUP-TF complex formed by combining the antibody with the biological sample.

A further aspect of the present invention is a method for measuring a COUP-TF promoter comprising the steps of combining COUP-TF with a nuclear extract from a biological sample; and measuring the amount of COUP-TF/promoter binding.

Another aspect of the present invention is a method for measuring the native COUP-TF binding ability in a biological sample comprising the steps of combining a COUP oligonucleotide with a biological sample; and measuring the amount of COUP oligonucleotide/COUP-TF complex formed.

In a preferred embodiment, the method of measuring COUP-TF levels, COUP-TF promoter and COUP-TF binding ability can be used to detect defects in the COUP-TF binding system that result in diabetes. Additionally, promoters which are associated with very low density lipoproteins (VLDL) gene and the pro-opiomelanocortin gene can also be assayed.

Additionally aspects of the present invention include a COUP-TF cDNA close of up to about 1.5 Kb, polyclonal and monoclonal antibodies to COUP-TF and a murine hybridoma which produces said monoclonal antibody.

Other and further objects, features and advantages will be apparent in the following description of the presently preferred embodiments of the invention given for the purposes of disclosure when taken in conjunction with the accompanying drawings.

Figure 1:
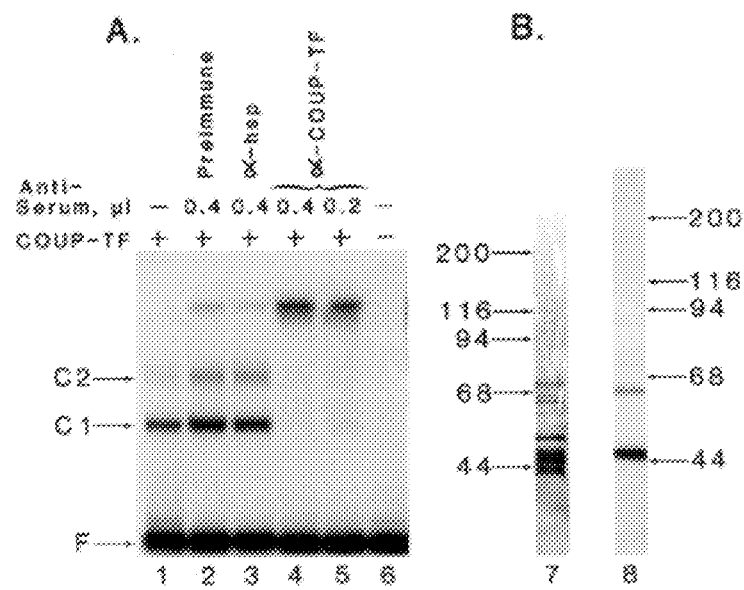
FIGS. 1a and b are examples of the use of gel retardation and Western blot analysis for the characterization of antiserum to COUP-TF.

The drawings and figures are not necessarily to scale and certain features of the invention may be exaggerated in scale or shown in schematic form in the interest of clarity and conciseness.

DETAILED DESCRIPTION

It will be readily apparent to one skilled in the art that various substitutions and modifications may be made to the invention disclosed herein without departing from the scope and spirit of the invention.

The term "oligonucleotide" as used herein, defines a molecule comprised of more than three deoxyribonucleotides or ribonucleotides. It's exact length will depend on many factors relating to the ultimate function and use of the oligonucleotide.

The term "functional" as used herein indicates that the molecules performs its normal function. For example, a functional gene is one which synthesizes a protein or fragment thereof, wherein the protein will function in its normal manner. Functional COUP-TF will bind to a promoter and cause the downstream gene to institute transcription of the protein.

The term "steroid receptor superfamily" refers to that class of Zn-finger proteins which include the steroid/thyroid hormone/vitamin receptor superfamily. This steroid hormone receptor superfamily consists of gene regulators which are proteins which bind and activate distal promoter elements of genes. Characteristic of this system are 20 invariant residues and 12 conserved residues. COUP-TF contain all 20 invariant residues and 11 of the 12 conserved residues. The only amino acid that differs from the conserved Zn-finger sequence is a glutamine which replaces a conserved lysine in the second finger. The insert of this clone was 1513 nucleotides in length. It contained an open reading frame of 1254 bases.

The term "native" means the unaltered molecule as isolated from a biological sample. This is in contrast to a synthesized or recombinant molecule or product of a synthesized or recombinant molecule.

The term "biological sample" as used herein means a sample taken from a living organism including man. For example, and not by way of limitation, it can include blood or its component parts, red blood cells, white blood cells, platelets, serum, tissue samples from skin, and organs, hair, urine, saliva, sweat, tears and amniotic fluids.

As used herein, the term "promoter" refers to a recognition site in a DNA strand to which a protein binds thereby initiating transcription. The promoter sequence is upstream from the gene to which it regulates.

As used herein, the term "hybridoma" means a hybrid cell resulting from the fusion of a specific antibody-producing spleen cell with a myeloma cell. The hybrid cell has the growth characteristics of the myeloma cell and the antibody secreting characteristics of the spleen cell.

One embodiment of the present invention is a method for measuring COUP-TF level in a biological sample comprising the steps of combining an antibody that binds to at least one antigenic site of COUP-TF with said biological sample; and assaying the biological sample/antibody mixture for antibody binding.

In one particular embodiment of the present invention, the assaying step includes measuring the antibody/COUP-TF complex formed in the combining step.

The antibodies used in the present invention can be polyclonal or monoclonal and specifically bind to at least one antigenic site of COUP-TF. The polyclonal antibodies were prepared by purification of COUP-TF from nuclear extracts of HeLa cells. The nuclear extract was fractionated sequentially on DEAE, phosphocellulose, Sephacryl S300 and Heparin-Sepharose column chromotography. The fractions containing COUP-TF were pooled and loaded onto a COUP sequence-specific affinity column, and the flow-through fraction was collected. COUP-TF is then eluted from the column with a buffer containing 0.6M NaCl.

Alternatively, the process can be facilitated by applying the HeLa nuclear extracts directly onto a sequence-specific DNA affinity column three consecutive times. This second procedure typically yields about 18 $\mu$g of purified COUP-TF from about one liter of packed HeLa cells.

The eluted proteins from the third passage on the affinity column were then injected into rabbits. Two injections of 10 $\mu$g of purified COUP-TF were made into New Zealand White rabbits. The first injection was carried out intradermally in complete Freund's adjuvant and a booster injection was given subcutaneously with incomplete adjuvant four weeks later. The rabbits were bleed and the antibodies were then collected at ten day intervals.

A murine hybridoma which produces a monoclonal antibody secifically immunoreactive with COUP-TF can be prepared by injecting the purified proteins from the HeLa cells into Balb/C mice every two weeks. After 4–8 weeks, spleen cells can be isolated and fused with mouse myeloma cells. The resultant fused hybrids can then be colonized and screened for reactivity against the native proteins using the dot immunoblot method. The reactive hybridomas can be subcloned. Those subclones appearing to produce single colonies can be retested by the dot immunoblot method. Said recloned hybridomas can be further subcloned into microtiter plates and/or flasks without feeder layer cells.

In order to produce large amounts of monoclonal antibody at higher antibody concentration, the hybridoma clones can be grown as ascites tumors in mice. After approximately one week of tumor growth the antibody can be purified from ascites fluid by biochemical fractionation procedures. The monoclonal antibody can be typed and purified. The purified monoclonal antibody is aliquotted and stored until used.

The antibody can be labeled with a variety of compounds including radioisotopes fluorescers, chemiluminescers, enzymes and antibodies. A variety of standard techniques can be used to measure the amount of COUP-TF. These include measurement of light conjugated radioactivity, color producing enzyme, fluorescence, autoradiography, induced assay, direct binding ELISA, competition ELISA, direct binding RIA, competition RIA, electrophoresis, competitive binding and other methods familiar to one skilled in the art.

Various factors, will affect the choice of label and assay. These include the effect of the label on the rate of antibody antigen binding, the type of assay, the sensitivity of the label, the ease of making the labelled compound, the ability to automate, available instrumentation, convenience and the like.

An additional aspect of the present invention is a method for determining COUP-TF inducible promoter comprising the steps of combining COUP-TF with a nuclear extract from a biological sample and measuring the amount of COUP-TF promoter binding. As discussed previously, a variety of standard labels and assay techniques can be used to measure COUP-TF/promoter binding.

The method of determining a COUP-TF inducible promoter can be used to examine promoters associated with a variety of genes. For example the promoters for the genes encoding insulin, VLDL and pro-opiomelanocortin and ovalbumin are all COUP-TF inducible. Thus if a promoter for any of these genes is modified, its ability to bind COUP-TF will be altered and this can be detected with this method.

Another aspect of the present invention is a method for determining the native COUP-TF binding ability in a biological sample comprising the steps of combining a COUP oligonucleotide with a biological sample; and measuring the amount of COUP oligonucleotide/COUP-TF complex formed. As discussed previously, a variety of standard labels and assay techniques can be used to measure the COUP oligonucleotide/COUP-TF complex.

Some examples of COUP oligonucleotides include, 5'-TATGGTGTCAAAGGTCAAACTT-3' 5'-CCAGGGG TCAGGGGGGGGGCTT-3' 5'-GGGGAAACAAAG CAGGACCTTTGACCCCT-3' 5'-GATCCAGGAAGGAA GGTCACGTCCAAGGCTCACCA-3' and fragments and derivatives thereof. These sequences correspond to the promoter recognition sites of ovalbumin, insulin, VLDL pro-opiomelanocortin, respectively.

The above methods of the present invention have a variety of applications. For example, the method for measuring the amount of COUP-TF in a biological sample with antibodies can be used to determine the over production or under production of COUP-TF. This can be used to detect COUP-TF disease. Furthermore, this can be used to diagnose diabetes in those invididuals who are unable to produce sufficient COUP-TF to bind the promoter for the insulin gene.

Another method to determine disease includes using the COUP-TF system to look for abnormal promoters. In this assay, a COUP-TF protein is combined with a promoter from a biological sample. If there is binding of the COUP-TF to the promoter, the binding or the measurement of the product synthesized from the structural gene downstream can be used to measure normal COUP-TF promoter binding. If there is a defective promoter there will be altered binding and thus the downstream transcription would be altered. This can be used to detect those forms of diabetes which result from defects in the promoter sequence.

An additional method is to measure for alterations in the COUP-TF protein which could result in diabetes. Normal promoter oligonucleotides, their fragments or derivatives can be combined with native COUP-TF. If the COUP-TF is normal, it will bind and the appropriate binding can be measured. However, if the COUP-TF protein is abnormal, for example a change in the sequence, this can be detected by showing an alteration in the binding. Thus, this assay can be used to detect those cases of diabetes which are caused by an abnormal COUP-TF protein.

In addition to binding to the insulin gene, the COUP-TF also binds to the promoters for the VLDL gene and the pro-opiomelanocortin gene. Diseases associated with abnormal function of these genes are diabetes, lipoprotein abnormalities (perhaps atherosclerosis) and neurogenic and adrenal disorders, respectively.

An additional aspect of the present invention is a cDNA clone of about 1.5 kilobase said clone codes for a fragment of the COUP-TF polypeptide.

A specific embodiment of the cDNA clone is a cDNA sequence shown in Table 1.

| 5'- 10 | 20 | 30 | 40 |
|---|---|---|---|
| AGCAGCTGGC | GAGATCCGCA | GGACGACGTG | GCCGGGGGCA |
| 50 | 60 | 70 | 80 |
| ACCCCGGCGG | CCCCAACCCC | GCAGCGCAGG | CGGCCCGCGG |
| 90 | 100 | 110 | 120 |
| CGGCGGCGGC | GGCGCCGGCG | AGCAGCAGCA | GCAGGCGGGC |
| 130 | 140 | 150 | 160 |
| TCGGGCGCGC | CGCACACGCC | GCAGACCCCG | GGCCAGCCCG |
| 170 | 180 | 190 | 200 |
| GAGCGCCCGC | CACCCCCGGC | ACGGCGGGGG | ACAAGGGCCA |
| 210 | 220 | 230 | 240 |
| GGGCCCGCCC | GGTTCGGGCC | AGAGCCAGCA | GCACATCGAG |
| 250 | 260 | 270 | 280 |
| TGCGTGGTGT | GCGGGGACAA | GTCGAGCGGC | AAGCACTACG |
| 290 | 300 | 310 | 320 |
| GCCAATTCAC | CTGCGAGGGC | TGCAAAAGTT | TCTTCAAGAG |
| 330 | 340 | 350 | 360 |
| GAGCGTCCGC | AGGAACTTAA | CTTACACATG | CCGTGCCAAC |
| 370 | 380 | 390 | 400 |
| AGGAACTGTC | CCATCGACCA | GCACCACCGC | AACCAGTGCC |
| 410 | 420 | 430 | 440 |
| AATACTGCCG | CCTCAAGAAG | TGCCTCAAAG | TGGGCATGAG |
| 450 | 460 | 470 | 480 |
| GCGGGAAGCG | GTTCAGCGAG | GAAGAATGCC | TCCAACCCAG |
| 490 | 500 | 510 | 520 |
| CCCAATCCAG | GCCAGTACGC | ACTCACCAAC | GGGGACCCCC |
| 530 | 540 | 550 | 560 |
| TCAACGGCCA | CTGCTACCTG | TCCGGCTACA | TCTCdCTGCT |
| 570 | 580 | 590 | 600 |
| GCTGCGCGCC | GAGCCCTACC | CCACGTCGCG | CTACGGCAGC |
| 610 | 620 | 630 | 640 |
| CAGTGCATGC | AGCCCAACAA | CATTATGGGC | ATCGAGAACA |
| 650 | 660 | 670 | 680 |
| TCTGCGAGCT | GGCCGCGCGC | CTGCTCTTCA | GCGCCGTCGA |
| 690 | 700 | 710 | 720 |
| GTGGGCCCGC | AACATCCCCT | TCTTCCCGGA | TCTGCAGATC |
| 730 | 740 | 750 | 760 |
| ACCGACCAGG | TGTCCCTGCT | ACGCCTCACC | TGGAGCGAGC |
| 770 | 780 | 790 | 800 |
| TGTTCGTGCT | CAACGCGGCC | CAGTGCTCTA | TGCCGCTGCA |

-continued

| | | | |
|---|---|---|---|
| 810 | 820 | 830 | 840 |
| CGTGGCGCCG | TTGCTGGCCG | CCGCCGGCCT | GCATGCCTCG |
| 850 | 860 | 870 | 880 |
| CCCATGTCTG | CCGACCGCGT | CGTGGCCTTC | ATGGACCACA |
| 890 | 900 | 910 | 920 |
| TCCGCATCTT | CCAGGAGCAG | GTGGAGAAGC | TCAAGGCGCT |
| 930 | 940 | 950 | 960 |
| ACACGTCGAC | TCAGCCGAGT | ACAGCTGCCT | CAAAGCCATC |
| 970 | 980 | 990 | 1000 |
| GTGCTGTTCA | CGTCAGACGC | CTGTGGCCTG | TCGGATGCGG |
| 1010 | 1020 | 1030 | 1040 |
| CCCACATCGA | GAGCCTGCAG | GAGAAGTCGC | AGTGCGCACT |
| 1050 | 1060 | 1070 | 1080 |
| GGAGGAGTAC | GTGAGGAGCC | AGTACCCCAA | CCAGCCCAGC |
| 1090 | 1100 | 1110 | 1120 |
| CGTTTTGGCA | AACTGCTGCT | GCGACTGCCC | TCGCTGCGCA |
| 1130 | 1140 | 1150 | 1160 |
| CCGTGTCCTC | CTCCGTCATC | GAGCAGCTCT | TCTTCGTCCG |
| 1170 | 1180 | 1190 | 1200 |
| TTTGGTAGGT | AAAACCCCCA | TCGAAACTCT | CATCCGCGAT |
| 1210 | 1220 | 1230 | 1240 |
| ATGTTACTGT | CTGGGAGCAG | CTTCAACTGG | CCTTACATGT |
| 1250 | 1260 | 1270 | 1280 |
| CCATCCAGTG | CTCCTAGACC | TTGGGCGCTT | CCCACCTGCC |
| 1290 | 1300 | 1310 | 1320 |
| CCGTCCCCCT | AGAGACTCAG | AGGACCCACC | TGGGCCAAGG |
| 1330 | 1340 | 1350 | 1360 |
| ACTCCAAAGC | CGCGGGGACA | CCGGGAAGTG | CAGCGGGCCA |
| 1370 | 1380 | 1390 | 1400 |
| GGCAGGCTGG | GTGGGAGGGA | GGAGGGCCGA | GACAGGAGCk |
| 1410 | 1420 | 1430 | 1440 |
| GCCCACCCAG | CAGAAATACA | ATCCGAGCTA | CAAAGCATGG |
| 1450 | 1460 | 1470 | 1480 |
| GAAAAAGAGA | CTCTTTTAGG | ATCAGATCTG | TGAGCACGTT |
| 1490 | 1500 | 1510 | 1520 |
| GGCCAGGAAA | AACAAAAAAA | CAAAAAAAAA | CCG-3' | and fragments and derivatives thereof, said fragments and derivatives coding for a functional COUP-TF.

Another embodiment of the present invention is a ligand for activation of the COUP-TF. This ligand is a protein which has an affinity to a C-terminal binding site in COUP-TF. The protein is synthesized or produced in the target cells in an autocrine regulatory fashion. The ligand binds to COUP-TF and activates COUP-TF by standard mechanism analogous to those known for hormones, such as steroids, thyroid hormone and vitamins. This ligand can be assayed by combining COUP-TF with a biological sample and measuring the COUP-TF/ligand binding as previously discussed.

The following examples are offered by way of illustration and not intended to limit the invention in any manner. In these examples, all percentages are by weight, if for solids and by volume if liquids, and all temperatures are in degrees Celsius unless otherwise noted.

EXAMPLE 1 cDNA Clone for COUP-TF

The clone was constructed from a library of randomly primed and oligo-dT primed cDNAs constructed in an λgt11 using poly(A)$^+$-mRNA from HeLa cells. The original library contains $6 \times 10^6$ independent recombinants and was used without amplification. In the primary screen, one million phage plaques were screened with antiserum to COUP-TF using I$^{125}$ protein A to detect positive clones. On secondary screening, the first filters were probed with antibodies; the replicate filters were probed with $^{32}$P-labeled catenated COUP sequence. Only one clone cross-reacted with both probes.

The clone was isolated and tested for specific binding to the authentic COUP sequence. Phage were transferred to a nitrocellulose filters and subsequently treated with 6M guanidine hydrochloride to denature the fusion proteins. The filters containing the phage fusion proteins were probed with various radiolabeled DNA probes. Catenated COUP sequence bound strongly to the fusion proteins, while non-specific, sonicated salmon sperm DNA did not detectably bind to the preparation.

Lysogenic cell extracts were prepared from this recombinant plaque, incubated with the DNA fragment containing the COUP sequence and assayed in a gel retardation assay. Several protein-DNA complexes were formed using IPTG-induced cell extracts but not using uninduced extracts (Lanes 1 and 2 in FIG. 2), indicating that the proteins encoded by the cDNA could bind to the DNA fragment containing the COUP sequence. Binding specificity was demonstrated further by competition analysis. The formation of complexes could be abolished using an unlabeled oligonucleotide corresponding to the wild-type COUP sequence (Lanes 3 and 4, FIG. 2), while a mutant oligonucleotide failed to compete at 50-fold or 100-fold molar excess (Lanes 5 and 6, FIG. 2).

Figure 3:
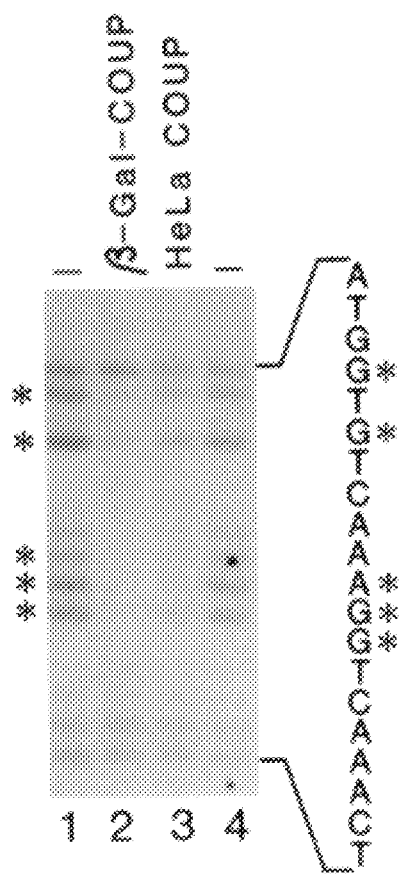
FIG. 3 shows methylation interference analysis of bacterially-synthesized COUP-TF.

The existence of multiple species of specific protein-DNA complexes were seen also by Western blot analysis. Three protein species in the size range of 130–165 kDa, COUP-TF fusion proteins containing 114 kDa of β-galactosidase, were found to interact with antiserum to COUP-TF in the induced cell extracts but not in the uninduced cell extracts. Furthermore, methylation interference analysis revealed that the purine contact sites of the fusion protein with the COUP sequence were identical to those found using HeLa COUP-TF (FIG. 3). These results support the conclusion that the bacterial fusion protein binds exactly as predicted to the COUP DNA sequence.

EXAMPLE 2

Amino Acid Sequence of the Protein Synthesized from COUP-TF cDNA

The nucleotide sequence is in Table 1 and the deduced amino acid sequence is shown in Table 2.

TABLE 2

Deduced Amino Acid Sequence of COUP-TF

SER —SER —TRP —ARG—ASP —PRO —GLN—ASP —ASP —VAL—ALA—GLY —GLY —ASN—PRO —

GLY —GLY—PRO —ASN—PRO —ALA—ALA—GLN—ALA—ALA—ARG—GLY—GLY—GLY—GLY—

GLY —ALA—GLY—GLU—GLN—GLN—GLN—GLN—ALA—GLY—SER —GLY—ALA—PRO —HIS —

THR —PRO —GLN—THR—PRO —GLY—GLN—PRO —GLY—ALA—PRO —ALA—THR—PRO —GLY—

THR —ALA—GLY—ASP —CYS —GLY—GLN—GLY—PRO —PRO —GLY—SER —GLY—GLN—SER —

GLN—GLN—HIS —ILE —GLU—CYS —VAL—VAL—CYS —GLY—ASP —LYS —SER —SER —GLY—

LYS —HIS —TYR—GLY—GLN—PHE —THR—CYS —GLU—GLY —CYS —LYS —SER —PHE —PHE —

LYS —ARG—SER —VAL—ARG—ARG—ASN—LEU —THR —TYR—THR —CYS —ARG—ALA—ASN—

ARG—ASN —CYS —PRO —ILE —ASP —GLN—HIS —HIS —ARG—ASN—GLN—CYS —GLN—TYR—

CYS —ARG—LEU —LYS —LYS —CYS —LEU —LYS —VAL—GLY—MET—ARG—ARG—GLU—ALA—

VAL—GLN—ARG—GLY—ARG—MET—PRO —PRO —THR—GLN—PRO —ASN—PRO —GLY—GLN—

TYR —ALA—LEU —THR—ASN—GLY—ASP —PRO —LEU —ASN—GLY—HIS —CYS —TYR—LEU —

SER —GLY—TYR—ILE —SER —LEU —LEU —LEU —ARG—ALA—GLU—PRO —TYR—PRO —THR—

SER —ARG—TYR—GLY—SER —GLN—CYS —MET—GLN—PRO —ASN—ASN—ILE —MET—GLY—

ILE —GLU—ASN—ILE —CYS —GLU—LEU —ALA—ALA—ARG—LEU —LEU —PHE —SER —ALA—

VAL—GLU—TRP —ALA—ARG—ASN—ILE —PRO —PHE —PHE —PRO —ASP —LEU —GLN—ILE —

THR —ASP —GLN—VAL—SER —LEU —LEU —ARG—LEU —THR —TRP —SER —GLU—LEU —PHE —

VAL—LEU —ASN—ALA—ALA—GLN—CYS —SER —MET—PRO —LEU —HIS —VAL—ALA—PRO —

LEU —LEU —ALA—ALA—ALA—GLY—LEU —HIS —ALA—SER —PRO —MET—SER —ALA—ASP —

ARG—VAL—VAL—ALA—PHE —MET—ASP —HIS —ILE —ARG—ILE —PHE —GLN—GLU—GLN—

VAL—GLU—LYS —LEU —LYS —ALA—LEU —HIS —VAL—ASP —SER —ALA—GLU—TYR—SER —

CYS —LEU —LYS —ALA—ILE —VAL—LEU —PHE —THR —SER —ASP —ALA—CYS —GLY—LEU —

SER —ASP —ALA—ALA—HIS —ILE —GLU—SER —LEU —GLN—GLU—LYS —SER —GLN—CYS —

ALA—LEU —GLU—GLU—TYR—VAL—ARG—SER —GLN—TYR—PRO —ASN—GLN—PRO —SER —

TABLE 2-continued

Deduced Amino Acid Sequence of COUP-TF

ARG—PHE—GLY—LYS—LEU—LEU—LEU—ARG—LEU—PRO—SER—LEU—ARG—THR—VAL—

SER—SER—SER—VAL—ILE—GLU—GLN—LEU—PHE—PHE—VAL—ARG—LEU—VAL—GLY—

LYS—THR—PRO—ILE—GLU—THR—LEU—ILE—ARG—ASP—MET—LEU—LEU—SER—GLY—

SER—SER—PHE—ASN—TRP—PRO—TYR—MET—SER—ILE—GLN—CYS—SER—

Since attempts to obtain N-terminal amino acid sequence from intact HeLa COUP transcription factor were not successful, polypeptides in the range of 46–48 kDa were obtained from a preparative SDS-PAGE gel and subjected to cyanogen bromide cleavage. After CNBr cleavage, the fragments were isolated by reverse phase HPLC. The amino acid sequences of five different polypeptide fragments were obtained from the 46 and 48 kDa polypeptides. Comparison of these peptide sequences with the amino acid sequence deduced from the cDNA clone confirmed the correct reading frame and provided additional strong evidence for the authenticity of the cDNA clone. It should be noted that the amino acid sequences of all five polypeptide fragments are preceded by methionine, the cleavage site of cyanogen bromide. We conclude that the clone we obtained encodes COUP-TF or at least one member of a closely related COUP-TF "family".

Although there was no direct evidence that the 43 and 44 kDa polypeptides were encoded from the same cDNA as the 46 and 46 kDa COUP-TF, the following suggested that they are closely related. The reverse phase HPLC elution profiles of CNBr-cleaved polypeptides of both species were indistinguishable. In addition, limited amino acid sequence analysis indicated that they share common peptides. Therefore, it is likely that all four 43–48 kDa polypeptides are either: (1) encoded by the same mRNA and represented covalently modified and/or partially degraded species, (2) generated from a single gene via alternate splicing, or (3) products of a closely related subfamily of genes. Our entire cDNA encodes for a 418 amino acid protein of 45.7 kDa. It represents virtually a full length clone for the 46–48 kDa COUP-TF species.

EXAMPLE 3

Estrogen Insensitivity

It is generally accepted that the Zn-finger domains (bases 241 to 438 in Table 1) of the receptors in the superfamily to which COUP-TF belongs are critical for DNA-binding. In light of the amino acid conservation within this region, it is likely that the DNA response elements recognized by the receptors may also be conserved. The DNA element recognized by COUP-TF contains a half-ERE site. Thus, the ability of the estrogen receptor to bind to the COUP sequence of the ovalbumin gene promoter can be tested with a vast excess of receptor. A 100-fold molar excess of COUP oligonucleotide could not complete for the binding of estrogen or progesterone receptors to their cognate response sequence. In addition DNase I footprinting reveals that the weak-binding pattern of estrogen receptor to COUP sequence is distinct from that of COUP-TF to COUP sequence. Finally, COUP sequence is not responsive to estrogen. This type of unproductive binding of one receptor to a response element of another receptor has been required. We conclude that COUP-TF is the physiologically important activator of the ovalbumin gene promoter.

EXAMPLE 4

Characterization of Antiserum to COUP-TF

Characterization of antiserum to COUP-TF by gel retardation and Western blot analyses can be seen in FIG. 1. Typically, 120 ml of nuclear extract was loaded at 0.25M NaCl on a 5 ml COUP-specific DNA affinity column. 0.6M NaCl eluate containing COUP-TF was adjusted to 0.3M salt and incubated with 300 μg/ml of Hinf I-digested pRB322 for 30 min prior to application to 2 ml of affinity resin. Repeat applications to the affinity column were carried out similarly except on the third cycle only 150 μg/ml of non-specific DNA competitor and 1 ml for affinity column resin were used. About 3.5 μg of COUP-TF were obtained. After accumulating 40 μg of proteins they were concentrated by heparin-Sepharose chromatography, lyophilized and used to generate antibody.

Partially purified HeLa COUP-TF was assayed in a gel retardation assay with pre-immune serum (Lane 2, FIG. 1), antiserum to heat shock protein (Lane 3, FIG. 1) and antiserum to COUP-TF (Lanes 4 and 5, FIG. 1). A DNA fragment spanning −269 to −44 of the ovalbumin gene (containing COUP sequence) was used as a probe. Lane 6, FIG. 1, contained probe alone. Binding reactions were carried out in the presence of 2 μg of Hinf I-digested pBR322 as a non-specific competitor. The bands corresponding to the free probe, the 43–48 kDa polypeptide-DNA complex and the 68 kDa polypeptide-DNA complex are indicated as F, C1 and C2 (FIG. 1), respectively.

A 0.42 μg aliquot of the COUP-TF from the third passage through the affinity column was precipated with trichloroacetate acid, subjected to an SDS-10% PAGE gel and stained with silver (Lane 7, FIG. 1). The size of each of the protein markers is given in kDa. In Lane 8, FIG. 1, a 140 μg aliquot of HeLa whose cell extract was run separately on an SDS-10% PAGE gel and transferred subsequently to an Immobilon PVDF Membrane. After blocking with 3% nonfat milk, the membrane was incubated with a 500-fold dilution of COUP-TF antiserum. $I^{125}$-protein A was used to visualize the signal.

EXAMPLE 5

COUP Sequence Binding to Fusion Protein

Figure 2:
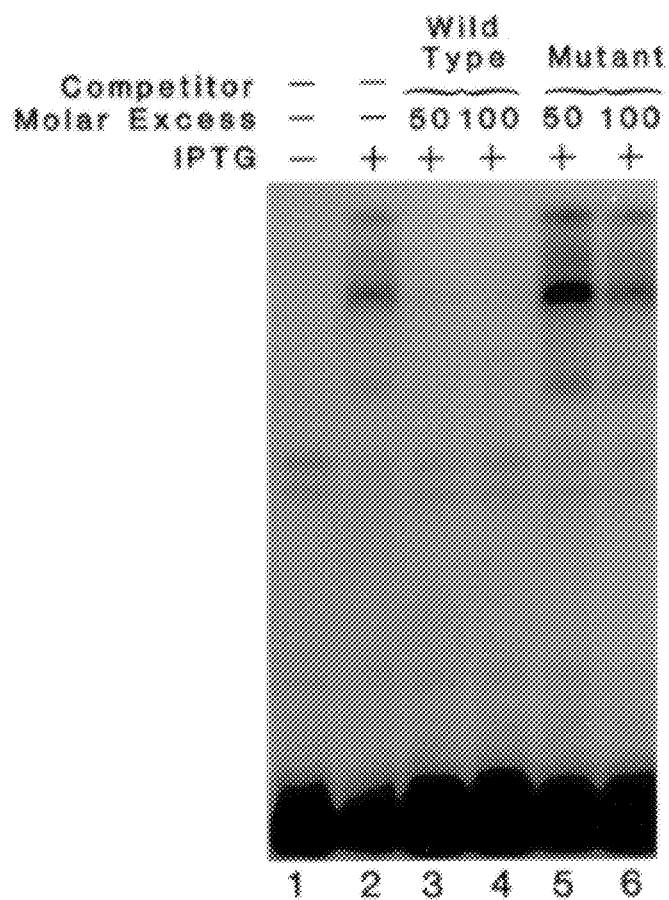
FIG. 2 shows the specific binding of bacterially-synthesized fusion protein to COUP sequence by competition analysis.

Specific binding to COUP sequence of bacterially-synthesized fusion protein is seen in FIGS. 2 and 3. HeLa COUP-TF was purified as described above. About 10 μg of protein was precipitated with 12% trichloroacetic acid and resolved in an SDS-10% PAGE gel. The gel was then stained with Coomassie blue. Since the 46 kDa and the 48 kDa polypeptides could not be separated, both peptides were excised and electroeluted concurrently. The 43 and 44 kDa COUP-TF peptides were processed in the same manner. The polypeptides were then subjected to CNBr cleavage in 70% formic acid in the dark at room temperature for 16 hours. Excess CNBr was removed by lyophilization. The digests were applied to an Aquapore RP-300 CB reverse phase HPLC column and eluted by a gradient of 0% to 64% acetonitrile containing 0.1% trifluoroacetic acid for 80 min at a flow rate of 0.6 ml/min. Polypeptides were sequenced on an Applied Biosystem model 477A protein sequenator equipped with the model 120A PTH-analyzer. The cDNA clone was restriction mapped by single or double digest. Restriction fragments subcloned into M13mp18 or M13mp19 were sequenced by dideoxy chain termination. Some fragments were sequenced by partial chemical degradation. GC-rich regions were sequenced with C7-deazadeoxyguanosine triphosphate mix substituted for the deoxyguanosine triphosphate mix.

Competition analysis was carried out by gel retardation assays. One μl of cell extract, from either uninduced cells (Lane 1, FIG. 2) or cells induced with IPTG (Lanes 2–6, FIG. 2), was incubated with 4 μg of Hinf I-digested pBR322 in 8 μl of transcription buffer (10 mM HEPES, pH 7.9, 100 mM KCl, 1 mM DTT, 0.05 mM EDTA, 2.5 mM $MgCl_2$, 6% glycerol and 2% ficoll) at room temperature for 10 min. Subsequently, 2 μl of labeled ovalbumin gene probe together with either double-stranded wild-type oligonucleotide (Lanes 3 and 4, FIG. 2) or double-stranded mutant oligonucleotide (Lanes 5 and 6, FIG. 2) were added into the mixture for 15 minutes before running on a 5% native polyacrylamide gel. The sequence of wild-type oligonucleotide, 5'-TCTATGGTGTCAAAGCT CAAACTTCTGA-3', corresponds to the sequence from −91 to −64 bases from the transcription start site of the ovalbumin gene. The mutant oligonucleotide was synthesized by making two C to G transversions at positions −74 and −81. The amounts of oligonucleotide added were shown as molar ratios of oligonucleotide to probe. For comparison, no oligonucleotide competitor was added in Lane 1 or Lane 2 (FIG. 2).

Methylation interference analysis of bacterially synthesized COUP-TF was performed. The β-galactosidase-COUP-TF fusion protein was purified using a sequence-specified DNA affinity column. The DNA fragment (−269 to −44) of the ovalbumin gene promoter, was methylated partially and used as a probe in a preparative gel retardation assay. Free probe (Lanes 1 and 4, FIG. 2b) and DNAs present in the retarded bands presenting complexes with HeLa COUP factor (Lane 3, FIG. 3) and bacterial expressed fusion protein (Lane 2, FIG. 3) were isolated. Each DNA band was then cleaved at the modified purine residues using alkali, and subjected to polyacrylamide gel electrophoresis under denaturing conditions. The asterisks indicate the purine contact sites.

EXAMPLE 6

Detection of Diabetes

A $^{32}$P-labeled oligonucleotide 5'-CCAGGGGTCAGG GGGGGGGTGCTT-3' will be used as a binding probe to detect COUP-TF in diabetic patients and healthy individuals. Conditions are as those described in Example 5. A defect in the regulation of the gene coding for COUP-TF will result in lower binding activity as compared to normal subjects. Another approach is to use COUP-TF cDNA as a probe to detect mRNA concentrations by Northern blot analysis. Reduced COUP-TF mRNA will indicate insufficient production of COUP-TF.

Also COUP-TF protein can be employed to test the integrity of the insulin gene promoter in normal versus diabetic patients. An insulin promoter fragment can be isolated or amplified using polymerase chain reaction (PCR) technology and employed in binding assays in vitro with COUP-TF. A mutation in the COUP promoter sequence would lead to poor COUP-TF binding and consequently poor insulin gene expression.

EXAMPLE 7

Defects in Very Low Density Apolipoprotein (VLDL)

A $^{32}$P-labeled oligonucleotide binding probe 5'GGGGAAACAAAGCAGGACCTTTGACCCCT-3 will be used to detect a deficiency in COUP-TF or a defect in the COUP-TF gene leading to lipoprotein abnormalities, and possibly, enhanced prediposition to development of atherosclerosis. Conditions and methods are as described in Example 6.

EXAMPLE 8

Detection of Defects in the Pro-Opiomelanocortin (POMC) System

A $^{32}$P-labeled oligonucleotide binding probe 5'-GAT CCAGGAAGGAAGGTCACGTCCAAGGCTCACCA-3' will be used to assess the level of COUP-TF and integrity of the POMC gene promoter. Conditions and methods are as described in Example 6. Abnormalities in POMC gene expression could lead to adrenal dysfunctions, eating disorders, and depressive or psychiatric disorders.

EXAMPLE 9

Defects in COUP-TF Activating Hormone

If a defect in the activating hormone (ligand) for COUP-TF is present, then COUP-TF will remain in the inactive form and malfunction of all genes regulated by COUP-TF will result. The presence of ligand can be detected and quantified by direct binding to the COUP-TF protein, using standard competitive assays.

EXAMPLE 10

Detection of COUP-TF Activating Hormone

COUP-TF can be produced in large quantities by inserting the cloned cDNA into a recombinant expression vector and transferring it to eucaryotic or procaryotic cells or transcribing and translating the COUP-TF cDNA in vitro. The recombinant produced protein (COUP-TF) can be tested for its binding affinity for a series of ligands (steroids, non-steroidal phenolic compounds, bioflavenoids, metaboic substrates and products, carbohydrate derivatives, etc.). If specific binding of any ligand is uncovered, using standard binding and competition assays, the ligand can be tested for its ability to activate COUP-TF in transfection assays with a reporter gene. If such ligand has demonstrable activation potential, chemically synthesized derivatives can be made (agonists and antagonists) which will have therapeutic potential for regulating all genes activated by COUP-TF. Such agents (drugs) may be used to treat human diseases which are in part the result of malfunction of genes regulated by COUP-TF.

One skilled in the art will readily appreciate the present invention is well adapted to carry out the objects and obtain the ends and advantages mentioned as well as those inherent therein. The methods, procedures and techniques described herein are presently representative of the preferred embodiments are intended to be exempliary and are not intended as limitations on the scope. Changes therein and other uses will occur to those skilled in the art which are encompassed within the spirit of the invention or defined by the scope of the appended claims.

What is claimed is:

1. A method for detection of diabetes comprising:

determining the native COUP-TF binding ability in a biological sample by purifying the COUP-TF from the biological sample to be tested;

adding the COUP oligonucleotide 5'-CCAGGGGTCAGGGGGGGGGTGCTT-3' to the purified COUP-TF; and measuring the amount of COUP oligonucleotide/COUP-TF complex formed.

2. A cDNA sequence of the formula:

| 5'- 10 | 20 | 30 | 40 |
|---|---|---|---|
| AGCAGCTGGC | GAGATCCGCA | GGACGACGTG | GCCGGGGGCA |
| 50 | 60 | 70 | 80 |
| ACCCCGGCGG | CCCCAACCCC | GCAGCGCAGG | CGGCCCGCGG |
| 90 | 100 | 110 | 120 |
| CGGCGGCGGC | GGCGCCGGCG | AGCAGCAGCA | GCAGGCGGGC |
| 130 | 140 | 150 | 160 |
| TCGGGCGCGC | CGCACACGCC | GCAGACCCCG | GGCCAGCCCG |
| 170 | 180 | 190 | 200 |
| GAGCGCCCGC | CACCCCCGGC | ACGGCGGGGG | ACAAGGGCCA |
| 210 | 220 | 230 | 240 |
| GGGCCCGCCC | GGTTCGGGCC | AGAGCCAGCA | GCACATCGAG |
| 250 | 260 | 270 | 280 |
| TGCGTGGTGT | GCGGGGACAA | GTCGAGCGGC | AAGCACTACG |
| 290 | 300 | 310 | 320 |
| GCCAATTCAC | CTGCGAGGGC | TGCAAAAGTT | TCTTCAAGAG |
| 330 | 340 | 350 | 360 |
| GAGCGTCCGC | AGGAACTTAA | CTTACACATG | CCGTGCCAAC |
| 370 | 380 | 390 | 400 |
| AGGAACTGTC | CCATCGACCA | GCACCACCGC | AACCAGTGCC |
| 410 | 420 | 430 | 440 |
| AATACTGCCG | CCTCAAGAAG | TGCCTCAAAG | TGGGCATGAG |
| 450 | 460 | 470 | 480 |
| GCGGGAAGCG | GTTCAGCGAG | GAAGAATGCC | TCCAACCCAG |
| 490 | 500 | 510 | 520 |
| CCCAATCCAG | GCCAGTACGC | ACTCACCAAC | GGGGACCCCC |
| 530 | 540 | 550 | 560 |
| TCAACGGCCA | CTGCTACCTG | TCCGGCTACA | TCTCGCTGCT |
| 570 | 580 | 590 | 600 |
| GCTGCGCGCC | GAGCCCTACC | CCACGTCGCG | CTACGGCAGC |
| 610 | 620 | 630 | 640 |
| CAGTGCATGC | AGCCCAACAA | CATTATGGGC | ATCGAGAACA |
| 650 | 660 | 670 | 680 |
| TCTGCGAGCT | GGCCGCGCGC | CTGCTCTTCA | GCGCCGTCGA |
| 690 | 700 | 710 | 720 |
| GTGGGCCCGC | AACATCCCCT | TCTTCCCGGA | TCTGCAGATC |
| 730 | 740 | 750 | 760 |
| ACCGACCAGG | TGTCCCTGCT | ACGCCTCACC | TGGAGCGAGC |
| 770 | 780 | 790 | 800 |
| TGTTCGTGCT | CAACGCGGCC | CAGTGCTCTA | TGCCGCTGCA |
| 810 | 820 | 830 | 840 |
| CGTGGCGCCG | TTGCTGGCCG | CCGCCGGCCT | GCATGCCTCG |
| 850 | 860 | 870 | 880 |
| CCCATGTCTG | CCGACCGCGT | CGTGGCCTTC | ATGGACCACA |
| 890 | 900 | 910 | 920 |
| TCCGCATCTT | CCAGGAGCAG | GTGGAGAAGC | TCAAGGCGCT |
| 930 | 940 | 950 | 960 |
| ACACGTCGAC | TCAGCCGAGT | ACAGCTGCCT | CAAAGCCATC |
| 970 | 980 | 990 | 1000 |
| GTGCTGTTCA | CGTCAGACGC | CTGTGGCCTG | TCGGATGCGG |
| 1010 | 1020 | 1030 | 1040 |
| CCCACATCGA | GAGCCTGCAG | GAGAAGTCGC | AGTGCGCACT |
| 1050 | 1060 | 1070 | 1080 |
| GGAGGAGTAC | GTGAGGAGCC | AGTACCCCAA | CCAGCCCAGC |
| 1090 | 1100 | 1110 | 1120 |
| CGTTTTGGCA | AACTGCTGCT | GCGACTGCCC | TCGCTGCGCA |
| 1130 | 1140 | 1150 | 1160 |
| CCGTGTCCTC | CTCCGTCATC | GAGCAGCTCT | TCTTCGTCCG |
| 1170 | 1180 | 1190 | 1200 |
| TTTGGTAGGT | AAAACCCCCA | TCGAAACTCT | CATCCGCGAT |

-continued

|  |  |  |  |
|---|---|---|---|
| 1210 | 1220 | 1230 | 1240 |
| ATGTTACTGT | CTGGGAGCAG | CTTCAACTGG | CCTTACATGT |
| 1250 | 1260 | 1270 | 1280 |
| CCATCCAGTG | CTCCTAGACC | TTGGGCGCTT | CCCACCTGCC |
| 1290 | 1300 | 1310 | 1320 |
| CCGTCCCCCT | AGAGACTCAG | AGGACCCACC | TGGGCCAAGG |
| 1330 | 1340 | 1350 | 1360 |
| ACTCCAAAGC | CGCGGGGACA | CCGGGAAGTG | CAGCGGGCCA |
| 1370 | 1380 | 1390 | 1400 |
| GGCAGGCTGG | GTGGGAGGGA | GGAGGGCCGA | GACAGGAGCA |
| 1410 | 1420 | 1430 | 1440 |
| GCCCACCCAG | CAGAAATACA | ATCCGAGCTA | CAAAGCATGG |
| 1450 | 1460 | 1470 | 1480 |
| GAAAAAGAGA | CTCTTTTAGG | ATCAGATCTG | TGAGCACGTT |
| 1490 | 1500 | 1510 | 1520 |
| GGCCAGGAAA | AACAAAAAAA | CAAAAAAAAA | CCG-3' | coding for a functional COUP-TF.

* * * * *